(12) United States Patent
Verschuren et al.

(10) Patent No.: US 8,797,028 B2
(45) Date of Patent: Aug. 5, 2014

(54) SENSOR DEVICE FOR TARGET PARTICLES IN A SAMPLE

(75) Inventors: Coen Adrianus Johannes Verschuren, Eindhoven (NL); Josephus Arnoldus Henricus Maria Kahlman, Tilburg (NL); Albert Hendrik Jan Immink, Eindhoven (NL); Mischa Megens, Eindhoven (NL); Jeroen Veen, Eindhoven (NL); Bart Michiel De Boer, Eindhoven (NL); Theodorus Petrus Henricus Gerardus Jansen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 924 days.

(21) Appl. No.: 12/738,317

(22) PCT Filed: Oct. 21, 2008

(86) PCT No.: PCT/IB2008/054329
§ 371 (c)(1),
(2), (4) Date: Apr. 16, 2010

(87) PCT Pub. No.: WO2009/053902
PCT Pub. Date: Apr. 30, 2009

(65) Prior Publication Data
US 2010/0259254 A1     Oct. 14, 2010

(30) Foreign Application Priority Data
Oct. 25, 2007 (EP) .................................. 07119248

(51) Int. Cl.
*G01R 33/02* (2006.01)
*G01N 33/00* (2006.01)
*G01N 21/55* (2014.01)

(52) U.S. Cl.
USPC ........................... 324/244; 422/68.1; 356/445

(58) Field of Classification Search
None
See application file for complete search history.

(56) References Cited

U.S. PATENT DOCUMENTS

| 5,641,640 A | 6/1997 | Hanning |
| 5,835,231 A | 11/1998 | Pipino |

(Continued)

FOREIGN PATENT DOCUMENTS

| WO | 9103728 A1 | 3/1991 |
| WO | 2005010542 A2 | 2/2005 |

(Continued)

OTHER PUBLICATIONS

Wakazono et al: "Intracellular Dynamics Observed by Mode Switching of Microscope With a Light Incidence TOT HE Interface at Alternate Angles Through the Ultra High NA Objective"; Imaging, Manipulation, and Analysis of Biomolecules, Cells and Tissues IV, Edited by Daniel L. Farkas, Dan V. Nicolau, Robert C. Leif, Proceedings of SPIE, vol. 6088, Jan. 2006, pp. 60881L-1-60881L6.

(Continued)

Primary Examiner — Jermele M Hollington

(57) ABSTRACT

A sensor device and a method for the determination of the amount of target particles at a contact surface adjacent to a sample chamber include detecting, by a detector, the target particles in the sample chamber by a sensor element, and providing at least one corresponding sensor signal. An evaluation unit determines the amount of target particles in a first zone at the contracts surface and in a second zone a distance away from the contact surface based on this sensor signal. In an optical measurement approach, frustrated total internal reflection taking place under different operating conditions, such as wavelength and/or angle of incidence, may be used to extract information about the first and second zones. In a magnetic measurement approach, different magnetic excitation fields may be used to excite magnetic target particles differently in the first and second zone.

13 Claims, 14 Drawing Sheets

(56) References Cited

U.S. PATENT DOCUMENTS

| | | | |
|---|---|---|---|
| 6,127,183 A | 10/2000 | Ivarsson et al. | |
| 6,191,853 B1 | 2/2001 | Yamaguchi et al. | |
| 6,462,809 B1 | 10/2002 | Ryan et al. | |
| 6,511,854 B1 | 1/2003 | Asanov et al. | |
| 6,838,051 B2 | 1/2005 | Marquiss et al. | |
| 6,956,651 B2 | 10/2005 | Lackritz et al. | |
| 7,033,542 B2 | 4/2006 | Archibald et al. | |
| 7,106,051 B2 | 9/2006 | Prins | |
| 7,158,224 B2 | 1/2007 | Montagu | |
| 2002/0109100 A1 | 8/2002 | Jackson, III et al. | |
| 2005/0048599 A1 | 3/2005 | Goldberg et al. | |
| 2005/0053974 A1 | 3/2005 | Lakowicz et al. | |
| 2005/0213204 A1 | 9/2005 | Kei | |
| 2006/0194327 A1* | 8/2006 | Kahlan et al. | 324/313 |
| 2007/0046943 A1 | 3/2007 | Van Wiggeren et al. | |
| 2008/0024118 A1* | 1/2008 | Kahlman et al. | 324/204 |
| 2009/0219012 A1* | 9/2009 | Nieuwenhuis et al. | 324/204 |
| 2010/0188076 A1* | 7/2010 | Kahlman et al. | 324/232 |
| 2010/0267165 A1* | 10/2010 | Bruls et al. | 436/501 |
| 2010/0328654 A1* | 12/2010 | Verschuren et al. | 356/237.2 |
| 2011/0001472 A1* | 1/2011 | Kahlman | 324/239 |
| 2011/0026030 A1* | 2/2011 | Schleipen et al. | 356/432 |
| 2011/0188030 A1* | 8/2011 | Verschuren et al. | 356/128 |
| 2012/0062219 A1* | 3/2012 | Craus | 324/228 |

FOREIGN PATENT DOCUMENTS

| | | |
|---|---|---|
| WO | 2005010543 A1 | 2/2005 |
| WO | 2005116661 A1 | 12/2005 |

OTHER PUBLICATIONS

Margraves et al: "Measurements of the Minimum Elevation of Nano-Particles by 3D Nanoscale Tracking Using Ratiometric Evanescent Wave Imaging"; Experiments in Fluids (2006), vol. 41, pp. 173-183.

Sudo et al: "Quick and Easy Measurement of Particle Size of Brownian Particles and Plankton in Water Using a Self-Mixing Laser"; Optics Express, Feb. 2006, vol. 14, No. 3, pp. 1044-1054.

* cited by examiner $$u_{cb} = u - \alpha u' \quad \alpha = \left.\frac{u}{u'}\right|_{z=1\mu m} = 0.29 \quad (14\text{-}1)$$

$$U = \int_{z=1\mu m}^{\infty} u_{cb}(z) \, dz = 9\mu V \quad (14\text{-}2)$$

$$e_{th,GMR} = 0.13 \cdot \sqrt{R_{GMR} \cdot 1/2} = 2.1 nV \quad (14\text{-}3)$$

$$e_{th} = e_{th,GMR} \cdot \sqrt{1+\alpha^2} = 2.1 nV \quad (14\text{-}4)$$

$$d = \frac{SNR \cdot e_{th}}{U} = \frac{2 \cdot 2.1 \cdot 10^{-9}}{9 \cdot 10^{-6}} = 5 \cdot 10^{-4} / \mu m^3 \quad (14\text{-}5)$$

$$U_1 = MXT + d \quad U_2 = \beta \cdot MXT + \alpha \cdot d \quad (14\text{-}6)$$

$$V_1 = U_1 + d \quad V_2 = U_2 + \alpha \cdot d \quad (14\text{-}7)$$

$$\alpha = \frac{V_2 - U_2}{V_1 - U_1} \quad (14\text{-}8)$$

$$U = 18\mu V, \; e_{th,GMR} = 2.1 nV, \; e_{th} = 3.0 nV, \; d = 3.4 \cdot 10^{-4} / \mu m^3 \quad (14\text{-}9)$$

$$U = 49\mu V, \; e_{th} = 5 nV, \; d = 2 \cdot 10^{-4} / \mu m^3 \quad (14\text{-}10)$$

FIG. 14

$$\langle N_s \rangle = N_{tot} \frac{V_s}{V_{tot}} \qquad (18\text{-}1)$$

$$r = \frac{\langle N_s \rangle}{\sigma_N^2} < 1 \qquad (18\text{-}2)$$

$$\phi(t) = \sigma_N^2 e^{-t/\tau} \qquad (18\text{-}3)$$

$$\sigma_r^2 = 6D\Delta t \qquad (18\text{-}4)$$

$$\tau = \frac{r^2}{6D} \qquad (18\text{-}5)$$

$$\tau = \frac{h^2}{2D} \qquad (18\text{-}6)$$

$$S_N(f) = \sigma_N^2 \frac{4\tau}{1 + (2\pi f \tau)^2} \qquad (18\text{-}7)$$

FIG. 18

SENSOR DEVICE FOR TARGET PARTICLES IN A SAMPLE

The invention relates to a method and a sensor device for determining the amount of target particles at a contact surface adjacent to a sample chamber in which the target particles can be provided. Moreover, it relates to the use of such a device.

The US 2005/0048599 A1 discloses an optical method for the investigation of microorganisms that are tagged with particles such that a (e.g. magnetic) force can be exerted on them. In one embodiment of this method, a light beam is directed through a transparent material to a surface where it is totally internally reflected. Light of this beam that leaves the transparent material as an evanescent wave is scattered by microorganisms and/or other components at the surface and then detected by a photodetector or used to illuminate the microorganisms for visual observation.

Moreover, a magnetic sensor device is known from the WO 2005/010543 A1 and WO 2005/010542 A2 (which are incorporated into the present application by reference) which may for example be used in a microfluidic biosensor for the detection of molecules, e.g. biological molecules, labeled with magnetic beads. The magnetic sensor device is provided with an array of sensor units comprising wires for the generation of a magnetic field and Giant Magneto Resistances (GMR) for the detection of stray fields generated by magnetized beads. The signal of the GMRs is then indicative of the number of the beads near the sensor unit.

Based on this situation it was an object of the present invention to provide alternative means for determining the amount of target particles in a zone of a sample chamber, particularly at a contact surface, with improved accuracy and reliability.

The sensor device according to the present invention serves for the determination of the amount of target particles at a contact surface adjacent to a sample chamber in which a sample with said target particles can be provided.

The term "target particle" comprises in this context any connected piece of material that shall be detected, for example a biological substance (biomolecule, complex, cell fraction, cell etc.). Preferably, the "target particle" comprises a substance of interest and an associated label particle (atom, molecule, complex, nanoparticle, microparticle etc.) which has some property (e.g. optical density, magnetic susceptibility, electrical charge, fluorescence, radioactivity, etc.) that can be detected, thus indirectly revealing the presence of the associated substance of interest. Moreover, the target particles to be determined may all be of the same type or of different types (e.g. different biomolecules).

The "sample chamber" is typically an empty cavity or a cavity filled with some substance like a gel that may absorb a sample substance; it may be an open cavity, a closed cavity, or a cavity connected to other cavities by fluid connection channels.

The "contact surface" is an interface between the sample chamber and another component, e.g. a transparent carrier or some (e.g. semiconductor) substrate, at which target particles can collect.

Finally, it should be noted that the "amount of target particles" may be expressed in various appropriate ways, for example as the absolute number or the overall mass of the target particles (in a given volume), or as a density (i.e. number or mass of target particles per unit area or volume).

The sensor device comprises the following components:

a) A sensor element for detecting target particles in the sample chamber and for providing at least one corresponding sensor-signal (wherein the term "sensor-signal" shall in the following be used as a unique reference to this particular signal of the sensor element). As will be illustrated with respect to preferred embodiments of the invention, the sensor element may achieve the detection of target particles by any suitable method or principle, for example by optical, magnetic, mechanical, acoustic, thermal and/or electrical measurements. The sensor-signal will typically be an electrical signal representing a scalar value that is related to the amount of target particles in some region of the sample chamber.

b) An evaluation unit for determining the amount of target particles in a "first zone" and in a different "second zone" based on the at least one aforementioned sensor-signal, wherein the "first zone" is by definition a sub-region of the sample chamber that is disposed immediately at the contact surface and wherein the "second zone" is by definition a sub-region of the sample chamber that is disposed a nonzero distance away from the contact surface, i.e. separated from the contact surface by some intermediate space. The first and the second zones will often be non-overlapping, though a limited amount of overlap may in general be allowed. Moreover, the amount of target particles in the first and/or the second zone may be determined directly or indirectly, i.e. the evaluation unit may provide values which immediately represent said amounts or values that only implicitly depend on said amounts. The evaluation unit may for instance provide a single output value which directly represents the amount of target particles in the first zone adjacent to the contact surface, wherein this value was determined by taking into account the amount of target particles in the second zone (e.g. as a correcting factor).

Finally it should be noted that the evaluation unit may be realized by dedicated electronic hardware, digital data processing hardware with associated software, or a mixture of both.

The described sensor device has the advantage that the amount of target particles is (directly or indirectly) evaluated in two different zones, namely a first zone adjacent to the contact surface—which is usually the zone of primary interest, e.g. if biological target molecules are bound to specific binding sites at the contact surface—and simultaneously in a different second zone. Due to its distance from the contact surface, the second zone provides information about the amount or concentration of target particles in the bulk sample. This information turns out to be very valuable in many cases, as the amounts of target particles in the two zones usually have a strong interdependence such that correct conclusions from the measurements require to take both amounts into account. In a competitive assay, in which biomolecules compete with binding sites at the contact surface for target particles, the amount of biomolecules can for example only correctly be determined if both the amounts of bound target particles (first zone) and free target particles (second zone) are known.

Particular realizations of the sensor device may take many different forms. One large group of realizations ("two sensor-signals approach") is characterized in that the sensor element provides at least two sensor-signals that are in a different way related or sensitive to the amount of target particles in the first zone and the second zone, respectively. Combining these at least two sensor-signals in an appropriate way may therefore reveal the amount of target particles in the first zone and/or the second zone. One straightforward realization of this approach would use a sensor element which can measure in the two zones with different sensitivities, e.g. providing a first sensor-signal measured with high sensitivity in the first zone and low sensitivity in the second zone and a second sensor-signal obtained vice versa.

In many embodiments of the aforementioned case, the evaluation unit may be adapted to determine a weighted difference of the at least two sensor-signals (or, equivalently, a linear combination of all sensor-signals). Thus a simple mathematical operation will often already be sufficient to extract the information one is interested in.

According to another embodiment of the invention, the sample chamber comprises an exclusion zone adjacent to a part of the contact surface that by definition cannot be entered by target particles. Covering also such an exclusion zone with the measurements of the sensor element may favorably pronounce differences between the first and second zone in the sensor-signal(s).

In the following, particular realizations of the "two sensor-signals approach" will be described in more detail that are based on optical measurements. In these embodiments, the sensor element comprises:

a) At least one light source for emitting two light beams, which are called "input light beams" in the following, such that they are totally internally reflected under different conditions at the contact surface, yielding corresponding "output light beams".

It should be noted that the distinction between the two input light beams may be purely conceptual, i.e. the photons emitted by one and the same light source may be assigned to a first or a second input light beam, respectively, according to some given criterion, e.g. their wavelength in case of a polychromatic light source.

The light source may for example comprise a laser or a light emitting diode (LED), optionally provided with some optics for shaping and directing the input light beams. Moreover, it should be noted that the occurrence of total internal reflection requires that the refractive index of the medium in which the input light beams propagate to the contact surface is larger than the refractive index of the material adjacent to the contact surface (usually the sample). This is for example the case if the medium of light propagation is made from glass (n=1.6-2) and the adjacent material is water (n=1.3). It should further be noted that the term "total internal reflection" shall include the case called "frustrated total internal reflection", where some of the incident light is lost (absorbed, scattered etc.) during the reflection process.

b) At least one light detector for determining the amount of light in the output light beams and for providing corresponding sensor-signals. The light detector may comprise any suitable sensor or plurality of sensors by which light of a given spectrum can be detected, for example photodiodes, photo resistors, photocells, a CCD chip, or a photo multiplier tube. The "amount of light" may for example be expressed by the light intensity of the output light beams in at least a part of their cross section.

Optical measurements with total internal reflection have the advantages that they can be made without physical contact to the sample, that they are independent of e.g. magnetic manipulations of the target particles, and that they can very well be restricted to a small volume adjacent to the contact surface.

The aforementioned restriction of the described optical measurements to a small volume at the contact surface is due to the fact that evanescent waves are generated during total internal reflection that penetrate exponentially decaying into the adjacent medium, i.e. the sample. The required different conditions under which the two input light beams are totally internally reflected will thus preferably be such that the evanescent waves have different decay distances (which are defined as the distance where the amplitudes of the evanescent waves have dropped to $1/e \approx 37\%$). The evanescent waves will then probe volumes of different thicknesses adjacent to the contact surface, which can be exploited to extract information about target particles in the first and second zone, respectively.

The two input light beams may preferably have different spectral composition and/or angles of incidence at the contact surface. These two parameters can readily be controlled and have a crucial influence on the decay distance of evanescent waves.

In the following, particular realizations of the "two sensor-signals approach" will be described in more detail that are based on a magnetic detection of "magnetic target particles", i.e. target particles which are magnetic or can be magnetized. The basic embodiment of such a magnetic sensor device comprises:

a) At least one magnetic field generator for generating at least two magnetic excitation fields of different configuration in the sample chamber. In this context, two magnetic fields are considered as being of "different configuration" if the vectors of their magnetic induction are within the sample chamber not simply proportional to each other with a single, global proportionality factor.

b) A magnetic sensor element for detecting magnetic reaction fields generated by magnetic target particles in reaction to the aforementioned magnetic excitation fields and for providing corresponding sensor-signals. The magnetic sensor element may comprise any device that is suited for the detection of magnetic fields, for example a coil, Hall sensor, planar Hall sensor, flux gate sensor, SQUID (Superconducting Quantum Interference Device), magnetic resonance sensor, magneto-restrictive sensor, or magneto-resistive sensor of the kind described in the WO 2005/010543 A1 or WO 2005/010542 A2, especially a GMR (Giant Magneto Resistance), a TMR (Tunnel Magneto Resistance), or an AMR (Anisotropic Magneto Resistance).

By providing magnetic excitation fields with different configurations, the described magnetic sensor device is able to detect target particles in a sample chamber with different sensitivity in the first and second zone, respectively.

The magnetic field generator may preferably comprise at least two conductor wires that can selectively be supplied with excitation currents for generating magnetic excitation fields and that have different geometrical arrangement with respect to the magnetic sensor element. Thus magnetic excitation fields of different configuration can readily be generated that allow to selectively probe the first and second zone.

In another embodiment, the magnetic sensor device may comprise pairs of conductor wires, wherein the conductor wires of each pair are arranged symmetrically with respect to the magnetic sensor element. Such a symmetrical arrangement has the advantage that certain undesired effects (e.g. cross talk) will mutually compensate.

Up to now it was only assumed about the contact surface that it is some interface towards the sample chamber where target particles can collect. In preferred embodiments of the invention, the contact surface will additionally comprise binding sites for target particles. The binding sites may for example be biological molecules (e.g. antibodies) to which certain target particles (e.g. antigens) can specifically bind. Besides immobilizing target particles at the contact surface for an easy detection, an important purpose of binding sites is therefore often the specific selection of particular molecules of interest out of a complex mixture.

In another embodiment of the invention, the sensor device may comprise a manipulation device for actively moving target particles. The manipulation device may particularly comprise a magnetic field generator, e.g. an electromagnet, for exerting magnetic forces (via field gradients) on magnetic target particles. The manipulation may for example be used to move target particles in an accelerated way to the contact surface.

In connection with a contact surface that is coated with binding sites, the aforementioned manipulation device may optionally be adapted to remove target particles that are not bound to binding sites from the sensitive region of the sensor element. Thus a washing process can be performed leaving only bound target particles in the region that can be surveyed by the sensor element.

In the following, another large group of realizations will be described in which the evaluation unit is adapted to evaluate the temporal course of the at least one sensor-signal ("temporal analysis approach"). This requires that at least two values of the sensor-signal obtained at different points in time are available (preferably, the sensor-signal will even be continuous or quasi-continuous over time). In these embodiments, information about the first zone and the second zone of the sample chamber will be extracted from the time-variance of the sensor-signal(s). It should be noted that the borders between the "two sensor-signals approach" and the "temporal analysis approach" are fluent and largely depend on the definition of the sensor-signal(s). Thus every sensor-signal with a temporal course may in a kind of de-multiplexing arbitrarily be divided into a first sensor-signal corresponding to a first time interval and a second sensor-signal corresponding to a second time interval. In the context of the present invention, the assumption of the "two sensor-signals approach" is preferred if the sensor element makes measurements under different operating conditions (e.g. with light of different wavelengths or with magnetic fields of different configuration), while the "temporal analysis approach" refers more to situations in which the reasons for signal variations lie within the sample (e.g. movements of target particles).

One first embodiment of the "temporal analysis approach" is linked to the above possibility to remove free (unbound) target particles from the sensitive region of the sensor element with a manipulation device. Thus the temporal course of the sensor-signal may correspond (i) at a first time instant to a situation in which unbound target particles are present and (ii) at a second time instant to a situation in which they are removed from the complete sensitive region of the sensor element, i.e. in which only target particles bound to binding sites at the contact surface are present. The measurements at the two time instants will therefore allow to derive the desired amounts of target particles in the first and second zone, respectively.

In another important realization of the "temporal analysis approach", the temporal evaluation of the sensor-signal takes place with respect to stochastic movements of the target particles. As these particles are typically microscopic entities like atoms, molecules, complexes, or cells, they will be prone to stochastic movements in the liquid sample which are known as "Brownian motion". These movements are usually different in the first and second zone, respectively, and may therefore be used to infer information about these zones. If target particles are for example bound in the first zone at the contact surface, their stochastic movements will approximately be zero there.

According to a preferred embodiment of the aforementioned sensor device, the evaluation unit may be adapted to determine the noise power of the sensor-signal (which is usually related to the amount of target particles in the second zone). This determination is optionally done after a high-pass filtering for removing slow variations (due e.g. to binding processes). The noise power of a time-variable signal s(t) with a mean value $<s>=0$ can be defined by the formula $$\sigma_s^2 = \langle s^2(t) \rangle$$

In another embodiment, the evaluation unit may be adapted to determine the average number of target particles in the second zone and the variance of this number. Because a clustering of target particles increases the variance, said clustering can be detected if both the average number and the variance are known.

More generally, the evaluation unit of the sensor device may be adapted to infer information about the amount of clustered target particles, about a coverage of the contact surface (e.g. by air bubbles), and/or about diffusion characteristics of the target particles. These are examples for parameters which may favorably be used to increase the accuracy of the measurements.

The invention further relates to a method for determining the amount of target particles at a contact surface adjacent to a sample chamber in which a sample with said target particles is provided, wherein the method comprises the following steps:
 a) Detecting target particles in the sample chamber and providing at least one corresponding sensor-signal with a sensor element.
 b) Directly or indirectly determining with an evaluation unit the amount of target particles in a first zone immediately at the contact surface and a second zone a distance away from the contact surface based on the at least one sensor-signal.

According to a first preferred embodiment of the method, at least two sensor-signals are provided that are in a different way sensitive to the amount of target particles in the first zone and the second zone, respectively.

In the aforementioned case, at least one of the sensor-signals may relate to a region of the sample chamber that is free of target particles. This region may for example be an exclusion zone that cannot be entered by target particles or a region of the sample chamber from which unbound target particles have been washed away.

In an optical measurement approach, the mentioned two sensor-signals may be derived from a frustrated total internal reflection with evanescent waves of different decay distances.

Alternatively, the two sensor-signals may be derived from magnetic reaction fields of magnetic target particles that were excited with magnetic excitation fields of different configuration.

Moreover, the temporal course of the at least one sensor-signal may be evaluated, particularly with respect to stochastic movements of the target particles.

The above embodiments of the method describe in general form the steps that can be executed with sensor devices of the kind described above. Reference is therefore made to the above description of the sensor devices for more information about the details, advantages and modifications of these methods.

The invention further relates to the use of the sensor device described above for molecular diagnostics, biological sample analysis, or chemical sample analysis, food analysis, and/or forensic analysis. Molecular diagnostics may for example be accomplished with the help of magnetic beads or fluorescent particles that are directly or indirectly attached to target molecules.

These and other aspects of the invention will be apparent from and elucidated with reference to the embodiment(s) described hereinafter. These embodiments will be described by way of example with the help of the accompanying drawings in which.

Figure 15:
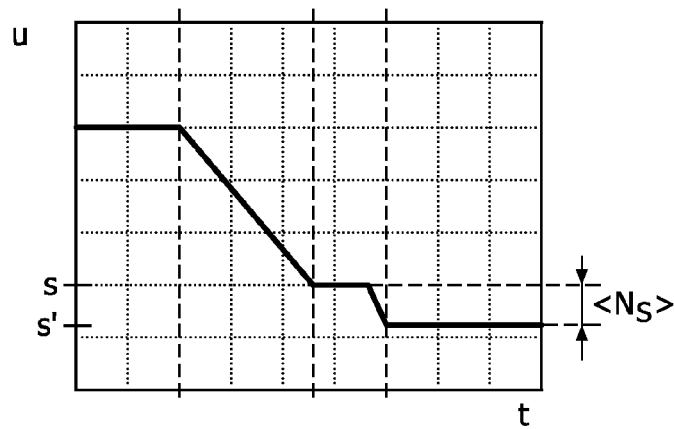
Figure 16:
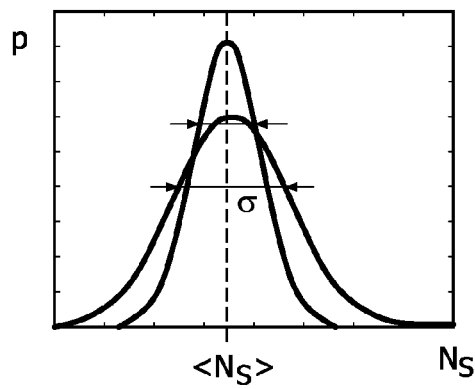
Figure 17:
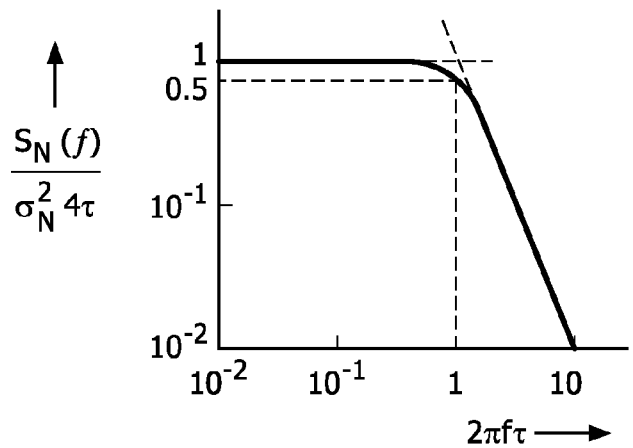

FIG. 14 summarizes various mathematical expressions relating to magnetic sensor devices;

FIG. 15 shows the normalized response of a sensor device during a typical assay with measurements before and after a washing step;

FIG. 16 illustrates the probability distribution of the number of single target particles in a given volume for two different degrees of clustering;

FIG. 17 shows the Lorentz spectrum;

FIG. 18 summarizes various mathematical expressions relating to the stochastic evaluation of sensor-signals.

Like reference numbers or numbers differing by integer multiples of 100 refer in the Figures to identical or similar components.

Biosensors can for example be used to test for road-side drugs of abuse in saliva. Drugs of abuse are generally small molecules that only possess one epitope and for this reason cannot be detected by a sandwich assay. A competitive or inhibition assay is the method to detect these molecules. A well-known competitive assay setup is to couple the molecules of interest onto a contact surface, and to prepare target particles by linking antibodies to a detection label (e.g. enzyme, fluorophore, or magnetic bead). This system is used to perform a competitive assay between the molecules of interest in the sample and on the surface, using the labeled antibodies (target particles). Evidently, the amount of bound target particles is related to the concentration of target particles that was added to the sample. As a consequence, the number of added target particles must be known a priori or be determined during the measurement for accurate, quantitative results.

The above scenario of a competitive assay illustrates in one example that the bulk concentration of target particles (the labels) in the volume above a sensor surface comprises valuable information. In general, measurements will usually have to be calibrated for the amount of target particles in solution. This amount is however often a-priori unknown due to varying redispersion properties of target particles dried in a cartridge. Various approaches to determine the amount of target particles in solution will therefore be explained in the following.

I. Two Sensor-Signals Approach with Optical Sensor Device Using FTIR

Figure 1:
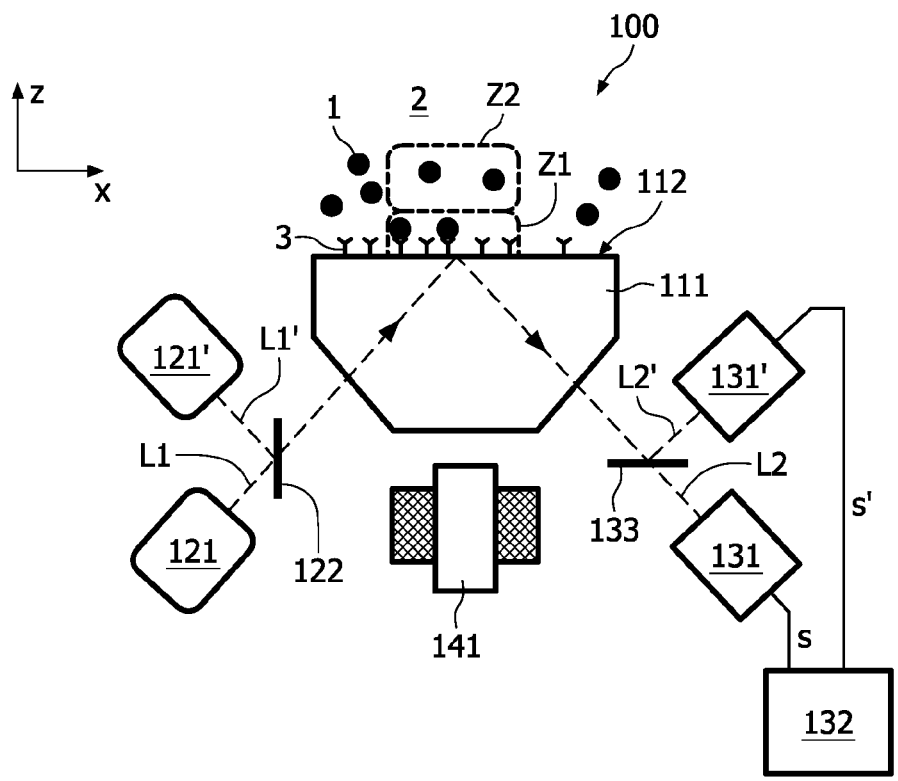
FIG. 1 shows schematically an optical sensor device according to the present invention that relies on frustrated total internal reflection.

FIG. 1 shows a general setup with a sensor device 100 according to the present invention. The setup comprises a carrier 111 that may for example be made from glass or transparent plastic like polystyrene. The carrier 111 is located next to a sample chamber 2 in which a sample fluid with target components to be detected (e.g. drugs, antibodies, DNA, etc.) can be provided. The sample further comprises magnetic particles, for example superparamagnetic beads, wherein these particles are usually bound as labels to the aforementioned target components. For simplicity only the combination of target components and magnetic particles is shown in the Figure and will be called "target particle 1" in the following. It should be noted that instead of magnetic particles other label particles, for example electrically charged or fluorescent particles, could be used as well.

The interface between the carrier 111 and the sample chamber 2 is formed by a surface called "contact surface" 112. This contact surface 112 is coated with capture elements 3, e.g. antibodies, which can specifically bind the target particles.

The sensor device comprises a magnetic field generator 141, for example an electromagnet with a coil and a core, for controllably generating a magnetic field at the contact surface 112 and in the adjacent space of the sample chamber 2. With the help of this magnetic field, the target particles 1 can be manipulated, i.e. be magnetized and particularly be moved (if magnetic fields with gradients are used). Thus it is for example possible to attract target particles 1 to the contact surface 112 in order to accelerate their binding to said surface, or to wash unbound target particles away from the contact surface before a measurement.

The sensor device further comprises a light source 121 that generates an input light beam L1 which is transmitted into the carrier 111 through an "entrance window". As light source 121, a laser or an LED, particularly a commercial DVD ($\lambda$=658 nm) laser-diode can be used. A collimator lens may be used to make the input light beam L1 parallel, and a pinhole of e.g. 0.5 mm may be used to reduce the beam diameter. The input light beam L1 arrives at the contact surface 112 at an angle θ larger than the critical angle $\theta_c$ of total internal reflection (TIR) and is therefore totally internally reflected in an "output light beam" L2. The output light beam L2 leaves the carrier 111 through another surface ("exit window") and is detected by a light detector 131. The light detector 131 determines the amount of light of the output light beam L2 (e.g. expressed by the light intensity of this light beam in the whole spectrum or a certain part of the spectrum). The corresponding sensor-signal s is evaluated and optionally monitored over an observation period by an evaluation and recording module 132 of an evaluation unit EU that is coupled to the detector 131.

It is possible to use the detector 131 also for the sampling of fluorescence light emitted by fluorescent particles 1 which were stimulated by the input light beam L1, wherein this fluorescence may for example spectrally be discriminated from reflected light L2. Though the following description concentrates on the measurement of reflected light, the principles discussed here can mutatis mutandis be applied to the detection of fluorescence, too.

The described sensor device 100 applies optical means for the detection of target particles 1. For eliminating or at least minimizing the influence of background (e.g. of the sample fluid, such as saliva, blood, etc.), the detection technique should be surface-specific. As indicated above, this is achieved by using the principle of frustrated total internal reflection (FTIR). This principle is based on the fact that an evanescent wave decays (exponentially dropping) into the sample 2 when the incident light beam L1 is totally internally reflected. If this evanescent wave then interacts with another medium like the bound target particles 1, part of the input light will be coupled into the sample fluid (this is called "frustrated total internal reflection"), and the reflected intensity will be reduced (while the reflected intensity will be 100% for a clean interface and no interaction). Depending on the amount of disturbance, i.e. the amount of target particles on or very near (within about 200 nm) to the TIR surface (not in the rest of the sample chamber 2), the reflected intensity will drop accordingly. This intensity drop is thus a direct measure for the amount of bound target particles 1.

The described procedure is independent of applied magnetic fields. This allows real-time optical monitoring of preparation, measurement and washing steps. The monitored signals can also be used to control the measurement or the individual process steps.

Advantages of the described optical read-out combined with magnetic labels for actuation are the following:

Cheap cartridge: The carrier 111 can consist of a relatively simple, injection-molded piece of polymer material.

Large multiplexing possibilities for multi-analyte testing: The contact surface 112 in a disposable cartridge can be optically scanned over a large area. Alternatively, large-area imaging is possible allowing a large detection array. Such an array (located on an optical transparent surface) can be made by e.g. ink jet printing of different binding molecules on the optical surface. The method also enables high-throughput testing in well-plates by using multiple beams and multiple detectors and multiple actuation magnets (either mechanically moved or electro-magnetically actuated).

Actuation and sensing are orthogonal: Magnetic actuation of the target particles (by large magnetic fields and magnetic field gradients) does not influence the sensing process. The optical method therefore allows a continuous monitoring of the signal during actuation. This provides a lot of insights into the assay process and it allows easy kinetic detection methods based on signal slopes.

Easy interface: No electric interconnect between cartridge and reader is necessary. An optical window is the only requirement to probe the cartridge. A contact-less read-out can therefore be performed.

Low-noise read-out is possible.

The sensor device 100 as it was described up to now was only used for the determination of target particles 1 in a "first zone" Z1 immediately adjacent to the contact surface 112. To enable the device to measure also bulk concentrations, i.e. to detect target particles 1 in a "second zone" Z2 that is a distance z>0 away from the contact surface 112, its sensor element SE is extended such that a second input light beam L1' is additionally sent into the carrier 111. This second input light beam L1' is generated by a second light source 121' and superposed to the first input light beam L1 with a dichroic mirror 122 or a beamsplitter. In FIG. 1, the wavelengths of the two input light beams L1, L1' shall be different. The corresponding output light beams L2, L2' that are generated at the contact surface 112 by FTIR and then leave the carrier 111 on identical paths can therefore be separated by another dichroic mirror 133 or a beamsplitter, wherein the second output light beam L2' is detected by a second light detector 131'. This second light detector 131' generates a corresponding second sensor-signal s' and sends it to the evaluation and recording module 132 of the evaluation unit EU.

Instead of separate detectors 131 and 131', also a single detector solution is possible (provided that the sensitivity of the detector is sufficient for all used wavelengths). To separate the different signal responses, time-division-multiplexing (TDM), frequency-division-multiplexing (FDM) or a combination of the two can be applied. Synchronous detection provides adequate signal separation in case of FDM. Moreover, a single light source could be used to generate a second wavelength with frequency doubling (e.g. using a non-linear crystal).

The described extension of the sensor device 100 is based on the fact that the field amplitude FA of the evanescent waves that are generated during TIR of the input light beams L1, L1' is a function of the distance z from the contact surface 112 according to the formula:

$$FA \propto \exp\left(-\frac{2\pi}{\lambda} \sqrt{n_A^2 \sin^2(\theta) - n_B^2} \cdot z\right) \quad (1)$$

with λ being the wavelength of the corresponding input light beam, θ its angle of incidence, and $n_A$ and $n_B$ the refractive indices of the respective associated media. Different depths of the sample medium adjacent to the contact surface 112 can therefore be probed if the first and second input light beams have at least two different parameters from the set of $\{n_A/n_B, \theta, \lambda\}$. As the ratio of refractive indices can only hardly be changed, the input light beams should preferably have at least a different combination of wavelength and incident angle, i.e. either different wavelength (as in FIG. 1), different angle, or both (as in FIG. 2). According to formula (1), this results in a difference in evanescent decay distance and thus in a different depth response.

Preferably, the input light beams L1, L1' are reflected from the same sensing area. From the respective signals s and s', both the surface concentration of the target particles in the first zone Z1 and their concentration in the second zone Z2 above the contact surface 112 can be determined. When using more than two different parameters, more detailed information can be extracted on the depth distribution.

Figure 2:
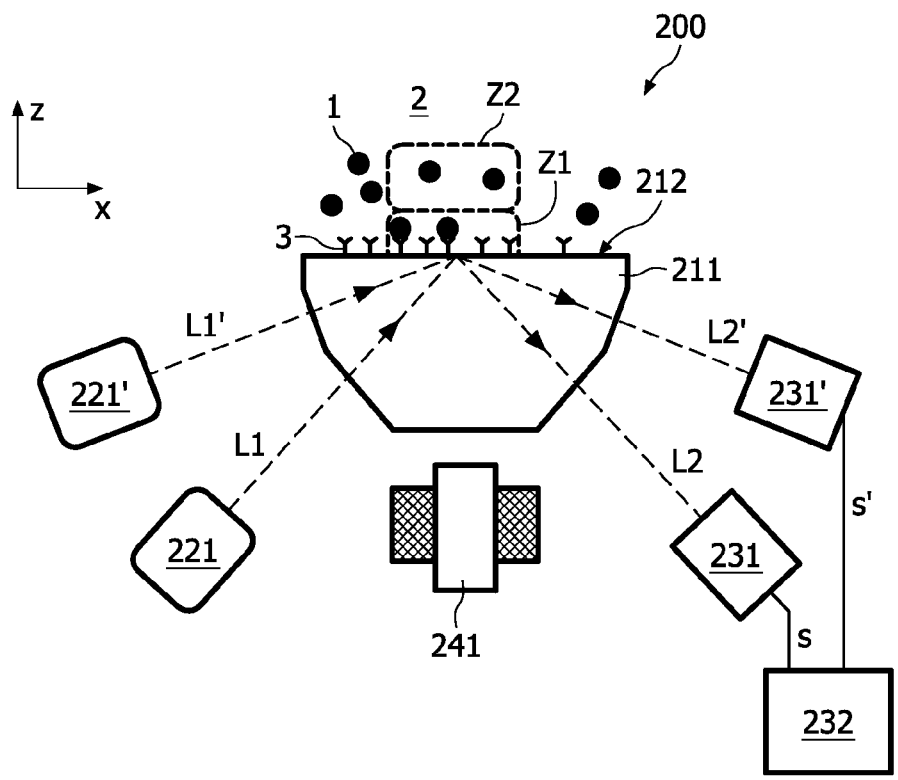
FIG. 2 shows a modification of the device of FIG. 1 in which input light beams with different angles of incidence are used.

FIG. 2 shows an alternative design of a sensor device 200 in which multiple angles θ of incidence are used in combination with a modified carrier 211 which provides multiple facets as perpendicular entrance and exit windows for the input light beams L1, L1' and the output light beams L2, L2'. Even limited angle scanning is possible, particularly if a hemispherical entrance and exit window of the carrier is used.

Instead of separate detectors 231, 231' for each output light beam L2 and L2', also a pixelated detector like a CCD or CMOS sensor could be used.

Moreover, a single, broad spectrum light source (e.g. white LED) may be used instead of reasonably monochromatic, independent light sources. By measuring the spectrum of the reflected output light beam, the target particle distribution can then be extracted (preferably in combination with a compensation in the form of a transmission measurement of the biological matrix). A color CCD may be used for detection. A more advanced solution would be to use a monochromator or similar construction, e.g. using a grating or prism to demultiplex the output light. In that case, a simple monochromatic (line-) CCD can be used for spatial detection of the spectrum. Detecting a 2D image for each detector and beam parameter provides information for constructing a 2D (x,y) target particle height distribution map.

Figure 3:
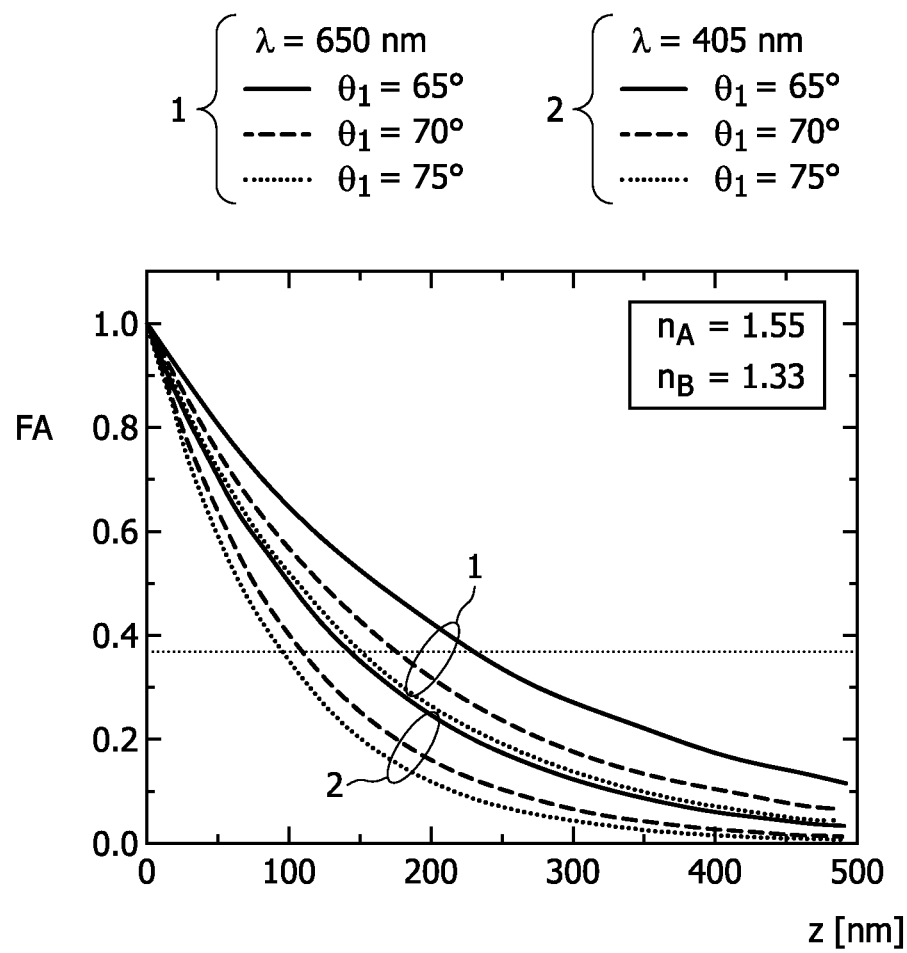
FIG. 3 shows the field amplitude as a function of the distance from the contact surface for evanescent waves of different wavelength and of different angles of incidence.
Figure 4:
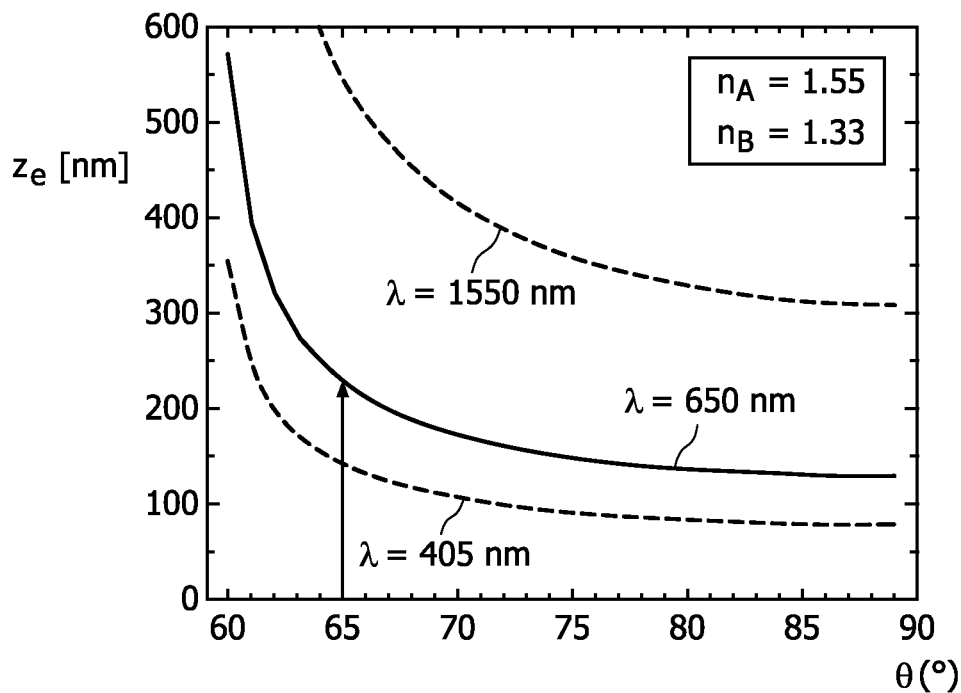
FIG. 4 shows the decay distance of evanescent waves in dependence on the angle of incidence for different wavelengths.

FIG. 3 depicts the normalized field amplitude FA of an evanescent wave extending from a medium A into a medium B (the sample) for two different wavelengths and three different angles of incidence. According to formula (1), the field amplitude FA decays exponentially with distance z. For larger wavelengths λ and smaller angles θ (i.e. closer to the critical angle), the decay is slower (also for smaller ratios of $n_A/n_B$). To characterize the decay distance, it is common to take the distance $z_e$ at which the field amplitude has decayed to 1/e times the amplitude at the interface (z=0). This 1/e level is depicted by the horizontal dashed line in FIG. 3. The corresponding distance $z_e$ is shown in FIG. 4 as a function of the angle θ of incidence. Clearly, angles θ close to (but larger than) the critical angle give the largest decay distance. It should be noted, however, that the closer the angle of incidence is to the critical angle, the larger the sensitivity to unwanted contamination and background particles in the sample liquid.

Figure 5:
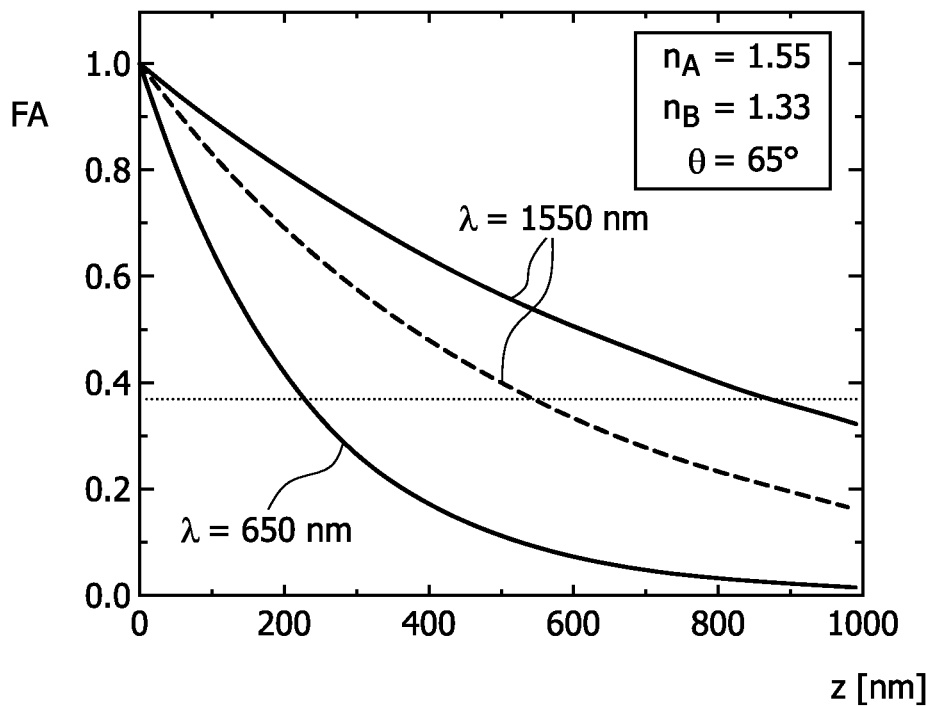
FIG. 5 shows in a diagram like that of FIG. 3 the field amplitude of evanescent waves in dependence on the distance from the contact surface for an angle of incidence of 65° and for two largely different wavelengths.

A typical size of magnetic beads used as labels in target particles is 300 nm. To detect these beads, a 650 nm laser at an incident angle θ of 65° can be used, corresponding to a decay distance $z_e$ of 228 nm for the mentioned refractive indices (FIG. 4). This is fine for detecting target particles at the contact surface in the first zone Z1, without any significant influence of beads further away from the surface. However, for detecting beads also further away from the contact surface, i.e. in the second zone Z2, a significantly larger range of evanescent waves is needed. This can be achieved by using a second light source with a much longer wavelength, e.g. 1550 nm. An example of evanescent field amplitude FA versus distance z from the contact surface is shown in FIG. 5 for this case. Clearly, the range can be extended to about 1 micrometer, especially when taking dispersion into account (cf. solid line for λ=1550 nm, with $n_{A,1550nm}$=1.50). It should be noted that the background signal originating from the biological matrix is still absent (or at least very small) due to its lower refractive index compared to the carrier material and the beads.

The signal response, i.e. the reduction in reflected intensity of the output light beams due to absorption and/or scattering/outcoupling from target particles, is directly related to the local field amplitude of the evanescent waves (integrated over the target particle distribution). Therefore, by measuring the signal response for each beam parameter, it is possible to extract information on the target particle distribution. This can for example be achieved by fitting the target particle distribution to the respective signal responses.

The following example illustrates this a bit further: the 650 nm curve in FIG. 5 only interacts significantly with the first 1 to 1.5 monolayers of magnetic beads. The corresponding signal will therefore only be sensitive for beads in the first zone Z1 at the contact surface. For the 1550 nm case, the situation is quite different: Beads at the contact surface will give a nearly equal response compared to 650 nm (although a somewhat larger signal is expected due to the larger average field amplitude from 0 to 300 nm), but the response for beads at a larger distance will be significantly larger due to the influence of the long exponential tail. Because the field amplitude profile is known in both cases, it is straightforward to determine the bead distribution corresponding to the measured signal responses. Clearly, the more (different) beam parameters and related signal changes are available, the more detailed the bead distribution can be determined.

II. Two Sensor-Signals Approach with Magnetic Sensor Device

A second approach for determining the concentration of target particles in a first and a second zone Z1 and Z2, respectively, is based on a magnetic sensor device comprising a magneto resistive sensor element, at least two conductive elements for generating a magnetic field in response to an excitation current applied in at least two excitation states, wherein the sensor responses originated from said excitation states are combined to a signal indicative to a target particle concentration in a volume above said sensor device. In further developments of that magnetic sensor device, an exclusion zone may prohibit target particles from entering a volume above the sensor surface. By generating at least two sensor responses as a result of at least two excitation states, the net response can be minimized for target particles at a given z-position above the sensor. In this way the response may be made zero for beads at- or above the sensor surface.

Figure 6A:
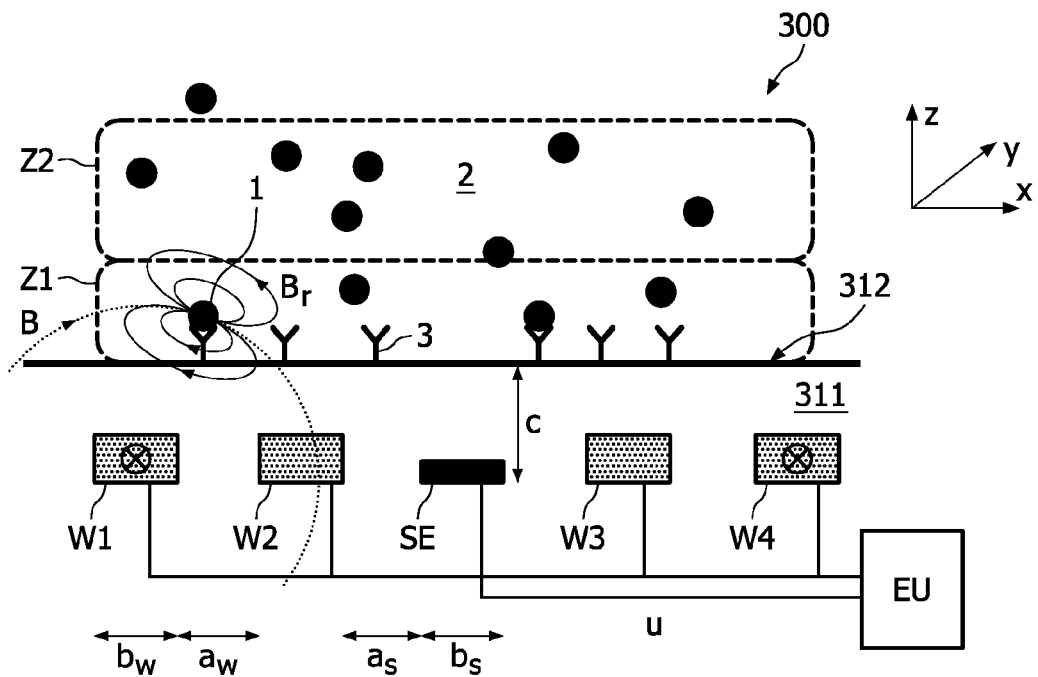
FIG. 6 shows (a) a first and (b) a second operating state of a magnetic sensor device with four conductor wires and a GMR sensor in one plane.
Figure 6B:
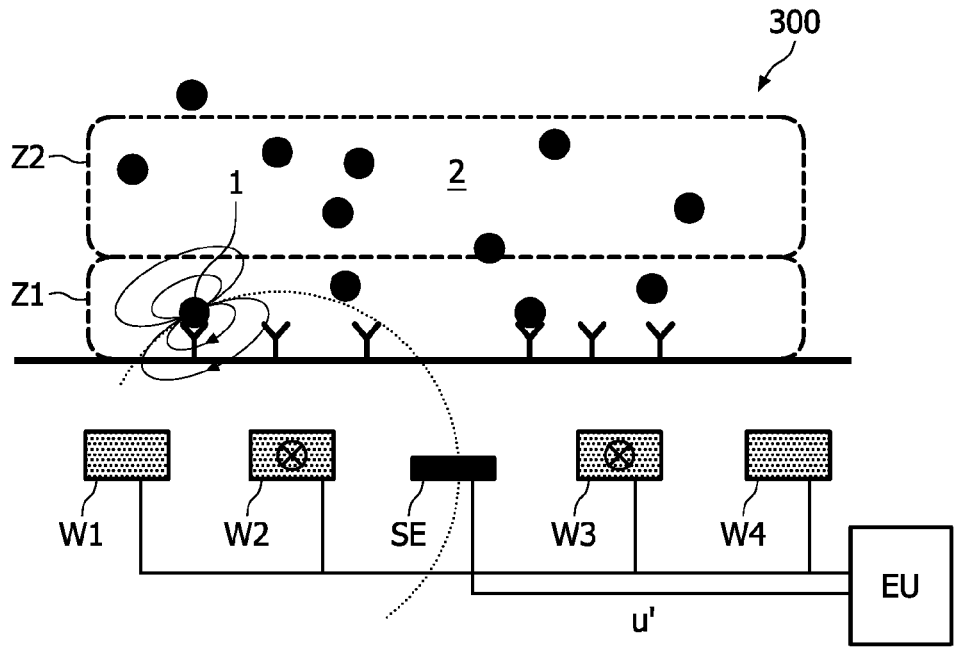

FIG. 6 illustrates a first embodiment of a magnetic sensor device 300 that realizes the above principles. The whole biosensor may typically consist of an array of (e.g. 100) sensor units of the kind shown in the Figure. The sensor device 300 comprises four conductor wires W1, W2, W3, W4 embedded in a substrate 311 in a common plane below a contact surface 312 towards a sample chamber 2. As above, the contact surface 312 is coated with binding sites 3 for target particles 1 that comprise magnetic beads as labels; for simplicity, the target particles 1 will simply be identified with the magnetic beads in the following. In the middle of the conductor wires W1-W4, a Giant Magneto Resistance (GMR) sensor element SE is disposed. Both the GMR element SE and the wires W1-W4 are connected to an evaluation unit EU that provides them with appropriate (excitation and sensor) currents and samples the measurement signals s, s' (i.e. the voltage drop across the GMR element SE).

FIG. 6 a) shows a first operating state of the sensor device 300 in which parallel excitation currents flow in the outer wires W1 and W4. This generates a first magnetic excitation field B which magnetizes the magnetic beads of the target particles 1 (for simplicity only the magnetic fields of one wire are drawn). The stray or reaction field $B_r$ from these magnetic beads introduces an in-plane magnetization component in the GMR element SE, which results in a measurable resistance change. If not stated otherwise, the widths $b_w$ of the wires, the width $b_s$ of the GMR element, the distances $a_w$ between the wires, and the distance $a_s$ between the wires and the GMR element are all equal in the shown magnetic sensors, with a typical value being about 3 µm. Furthermore, the common bottom of the wires and the GMR element is a distance of about c=1 µm below the contact surface 312.

Figure 7A:
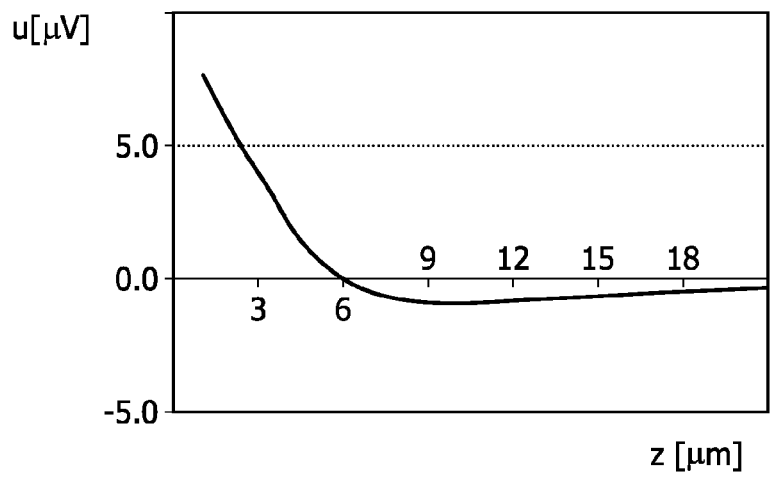
FIG. 7 shows the measurement signals of the magnetic sensor device of FIG. 6 in dependence on the distance from the contact surface in (a) the first operating state and (b) the second operating state as well as (c) the weighted difference of these data.
Figure 7B:
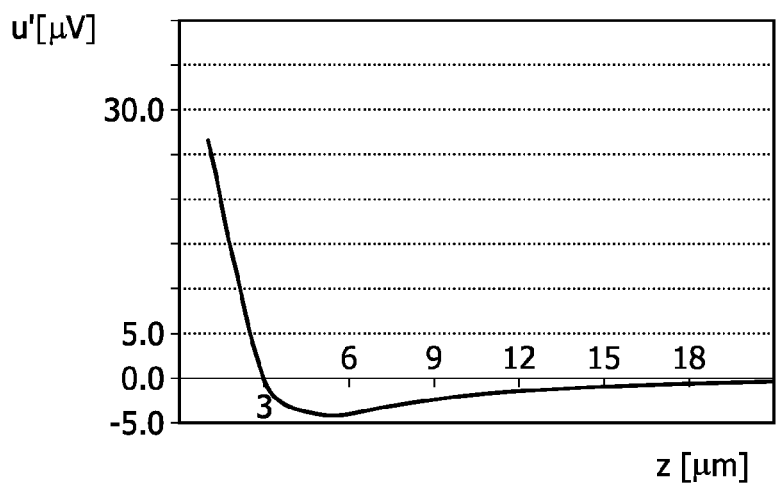
Figure 7C:
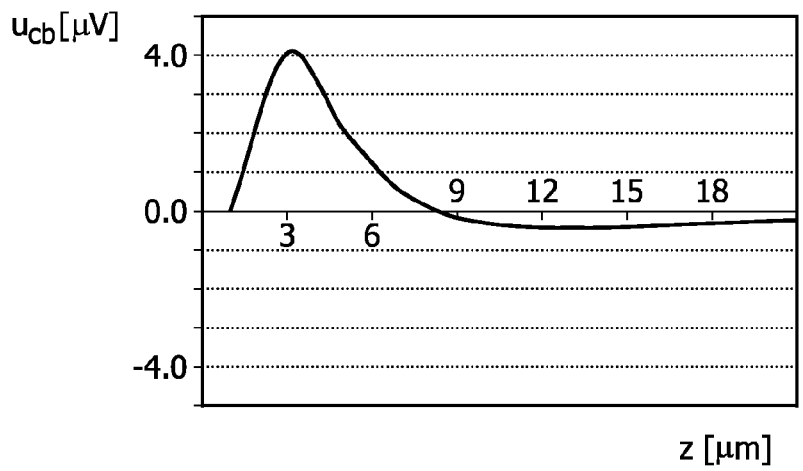

FIG. 7 a) shows for the first operating state the normalized response u of the GMR element to a bulk concentration of beads as a function of the vertical position z (with the following parameters: uniform bulk density of 1 bead/µm³; 200 nm Ademtech beads; GMR length 100 µm; GMR sensitivity 0.003 Ωm/A; excitation current of 25 mA in W1, W4; sensor current of 5 mA in GMR; the currents are chosen such that the total thermal dissipation is 25 mW).

FIG. 6 b) shows a second operating state of the sensor device 300 in which excitation currents flow in the inner wires W2 and W3 under the same residual parameters as in the first state. FIG. 7 b) shows the resulting normalized sensor response u' in a diagram like that of FIG. 7 a).

A new signal $u_{cb}$ can then be calculated by a weighted subtraction of the two sensor responses u and u' according to the formula (14-1) of FIG. 14. This signal is depicted in FIG. 7 c) and shows a sensitive volume between 2-9 µm above the contact surface.

The GMR voltage as a response to the total amount of beads amounts to the value U of formula (14-2). The thermal noise floor $e_{th,GMR}$ of the $R_{GMR}$=500 ΩGMR in a 1 s-measuring interval per state is given in formula (14-3). As a result the noise floor $e_{th}$ after weighted subtraction is as in formula (14-4). This brings the volume density d (beads per volume) for achieving 6 dB signal-to-noise ratio SNR (a factor of 2) in a 2 s measuring interval to the value of formula (14-5).

For didactic reasons the subtraction of the normalized voltages was described, which will obviously not be the case in a real implementation where the GMR voltages in the two states are weighted subtracted.

It should further be noted that other excitation schemes comprising e.g. anti-parallel currents, other geometries and other numbers of wires (at different z-position) may lead to the same objective. Some of these modifications will be considered in more detail below. Furthermore the same technique may be used to suppress the bulk response.

The strong advantage of the explained approach is that it measures the surface density (first region Z1) and the bulk density (second region Z2) at the same physical location where liquid flow is well controllable and sufficiently high. Furthermore no surface patterning is needed, which avoids extra costs and hindering of the micro fluidic flow.

The subtraction weight a of equation (14-1) can be found based on the following considerations: Beside the response to magnetic beads, the GMR element SE also comprises a magnetic crosstalk (MXT) signal component due to in-plane magnetic fields generated by the excitation wires W1-W4. As a result the GMR signals $U_1$, $U_2$ in the two measurement states are as expressed by equation (14-6), wherein d is the bead density and wherein the factors $\alpha$ and $\beta$ both are geometry dependent and may vary due to production process variations. If desired these factors can be obtained in the following two-step calibration procedure, either for a whole batch of sensors or for individual sensors prior to use:

1. Without beads (d=0) the sensor signals $U_1$, $U_2$ in both states are measured.
2. After applying a uniform surface bead density by e.g. sedimentation, the observed sensor signals $V_1$, $V_2$ in both two states are given by (14-7), from which the factor cc follows as in equation (14-8).

Figure 8A:
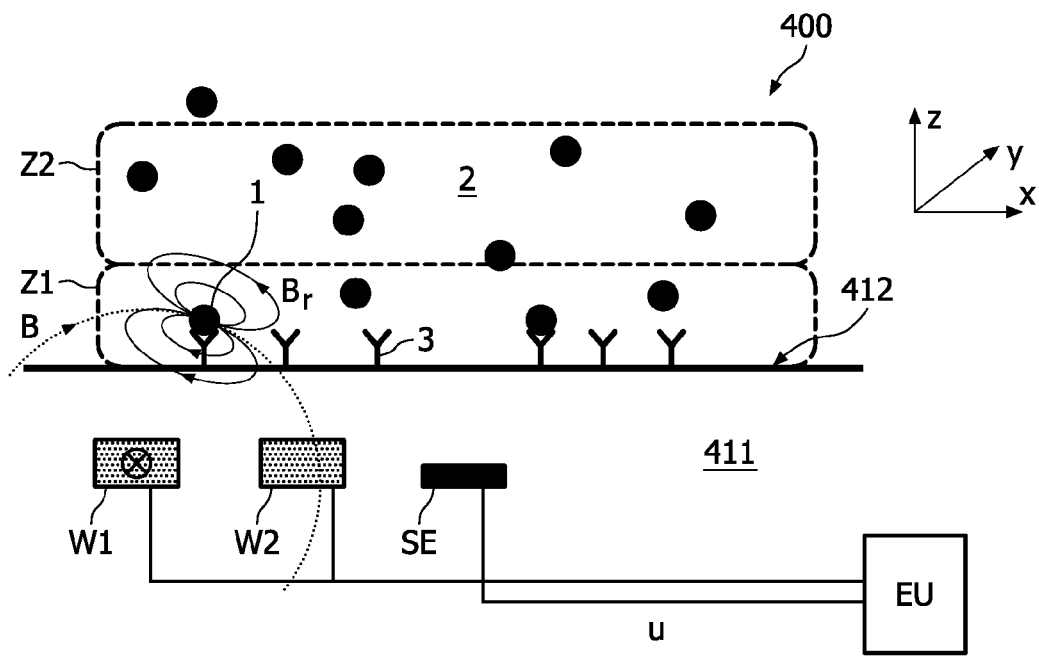
FIG. 8 shows (a) a first and (b) a second operating state of a magnetic sensor device with two conductor wires on one side of a GMR sensor.
Figure 8B:
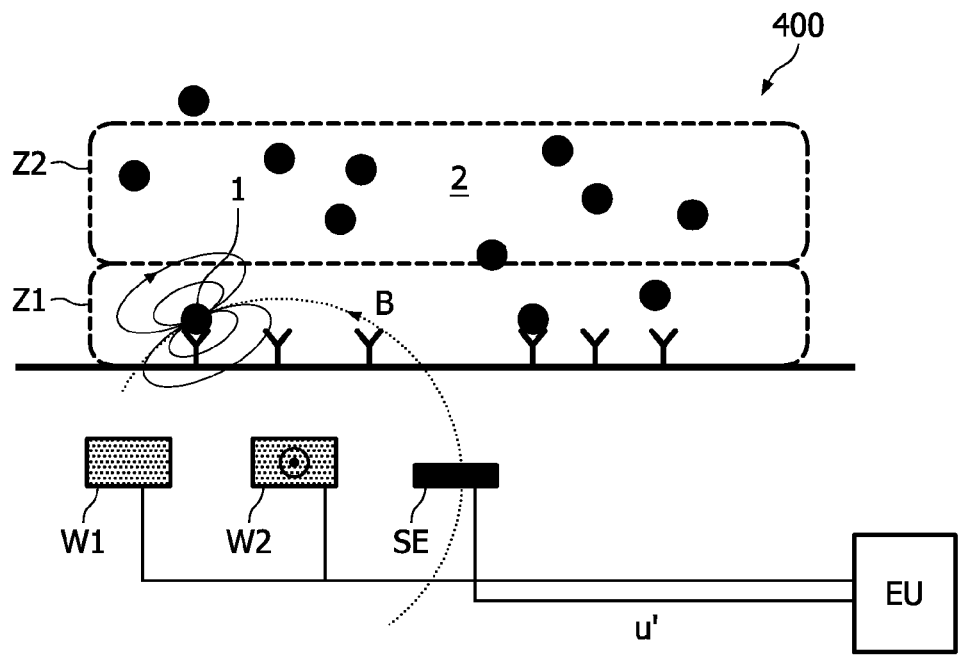

FIG. 8 shows as a variation a sensor device 400 that comprises only two excitation wires W1 and W2 on the same side of the GMR element SE, which are sequentially excited with oppositely directed currents in state 1 and state 2, respectively. The evaluation of the resulting sensor signals can be done as above.

Figure 9A:
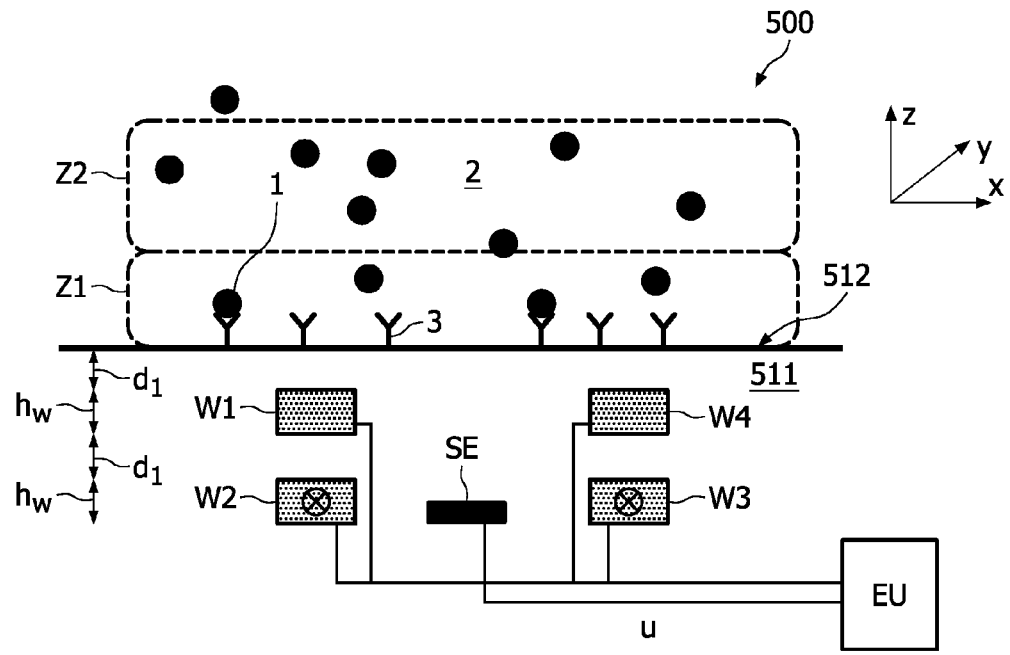
FIG. 9 shows (a) a first and (b) a second operating state of a magnetic sensor device with four conductor wires arranged in two parallel planes.
Figure 9B:
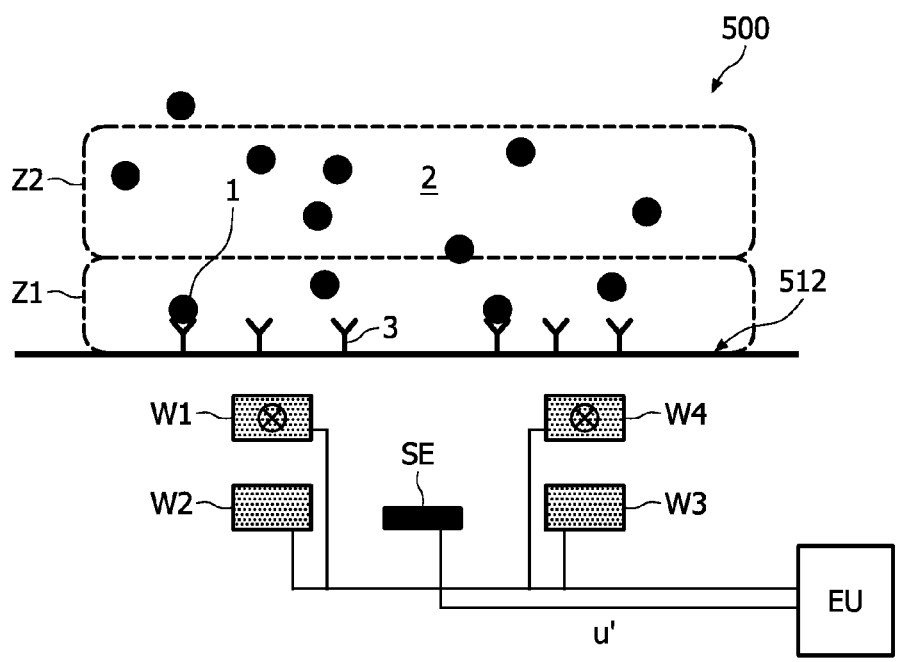

In the embodiment of a magnetic sensor device 500 shown in FIG. 9, two metal layers with four wires W1-W4 are used. In the first state of FIG. 9 a), the lower wires W2 and W3 are excited, while in the second state of FIG. 9 b) the upper wires W1 and W4 are excited. Typical values for the height of the wires are $h_w$=0.35 µm, and for their distance form each other and/or the contact surface $d_1$=0.5 µm.

Figure 10A:
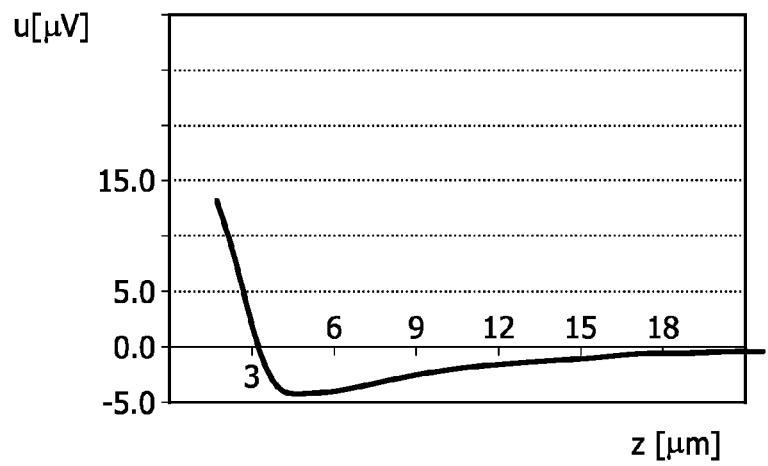
FIG. 10 shows the measurement signals of the magnetic sensor device of FIG. 9 in dependence on the distance from the contact surface in (a) the first operating state and (b) the second operating state as well as (c) the weighted difference of these data.
Figure 10B:
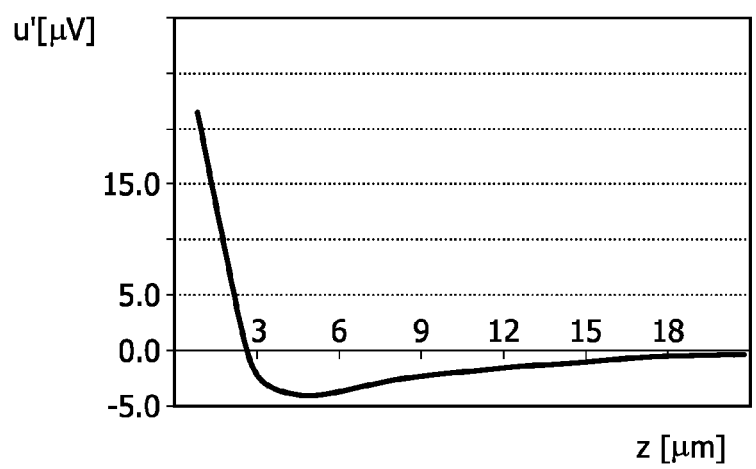
Figure 10C:
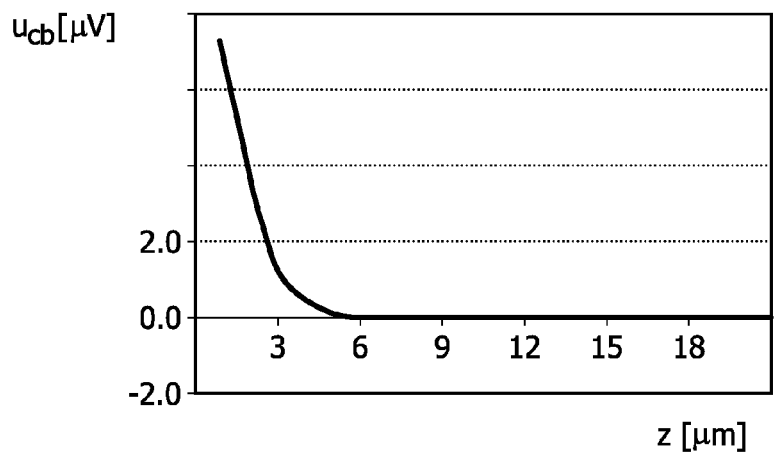

FIGS. 10 a) and b) show (similar to FIG. 7 and with the same parameters) the corresponding normalized GMR voltages u and u'. The weighted subtraction of these values (cf. equation (14-1)) with a factor of $\alpha$=1.05 yields the combined response $u_{cb}$ of FIG. 10 c), which shows a sensitive volume from 1.7 to 5 µm above the sensor.

The same calculations as in equations (14-2) to (14-5) yield for this case the values given in (14-9).

Figure 11:
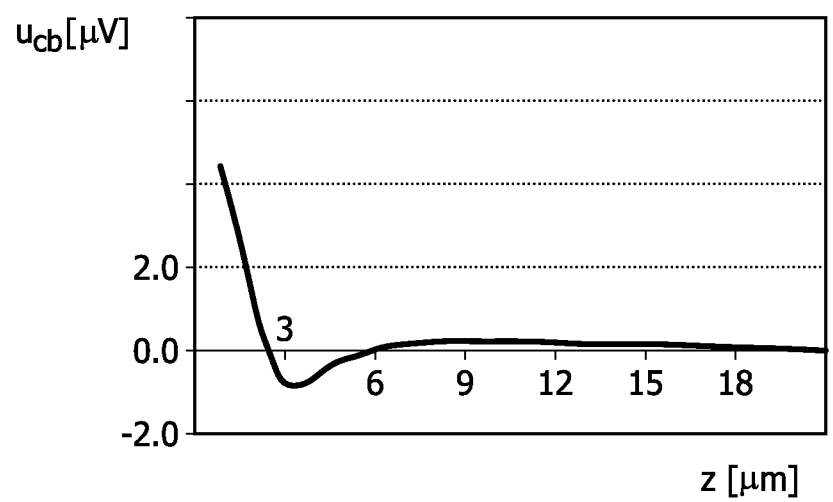
FIG. 11 shows a diagram corresponding to FIG. 10 c) in case of other geometrical parameters.

By increasing the spacing $a_s$ between the wires W2/W3 and the GMR element SE from 3 µm (FIGS. 9, 10) to 4 µm, the sensitive volume can even further be decreased. FIG. 11 shows in a diagram comparable to that of FIG. 10 c) how the combined net bulk response $u_{cb}$ for homogeneous bulk density is made zero, as the sensitive height is limited from 1.7 to 2 µm. Obviously many variations are possible on this theme.

Figure 12A:
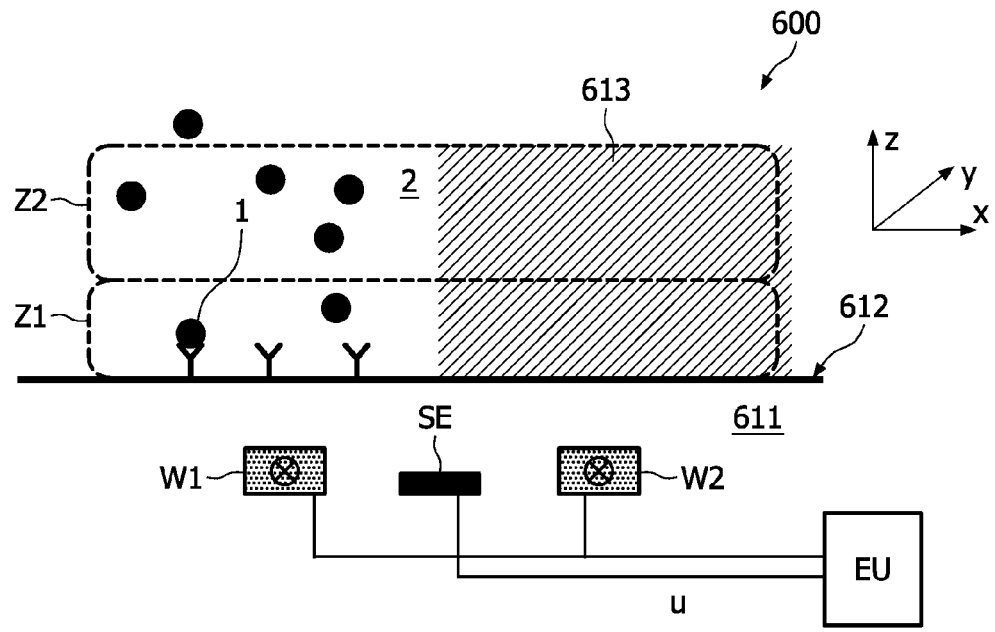
FIG. 12 shows (a) a first and (b) a second operating state of a magnetic sensor device with two wires and a GMR sensor in one plane and an exclusion zone half-way above them.
Figure 12B:
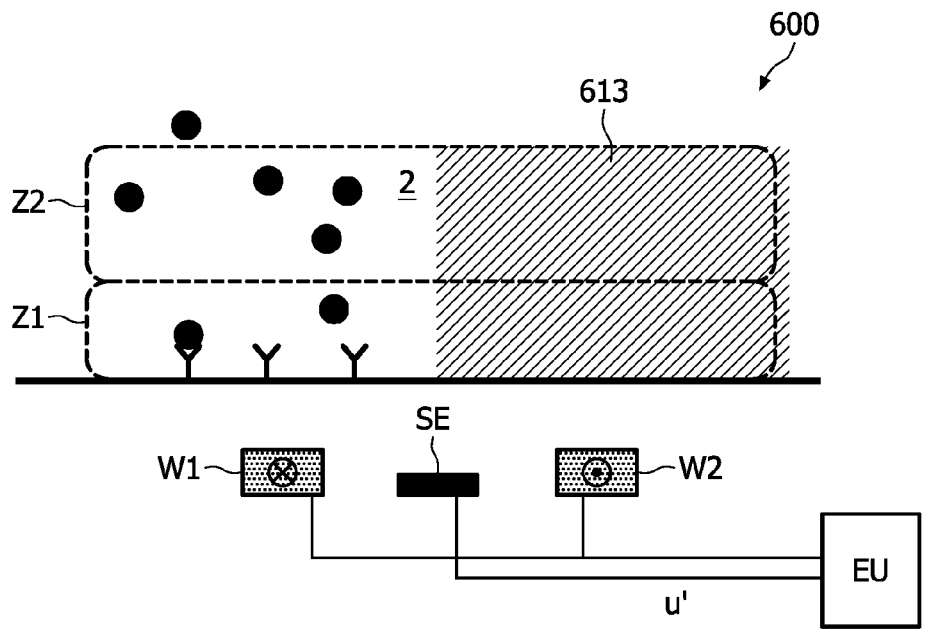
Figure 13A:
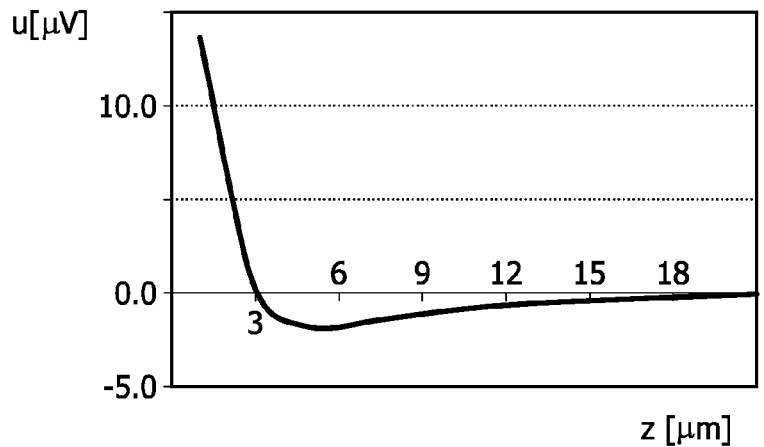
FIG. 13 shows the measurement signals of the magnetic sensor device of FIG. 12 in dependence on the distance from the contact surface in (a) the first operating state and (b) the second operating state as well as (c) the weighted difference of these data.
Figure 13B:
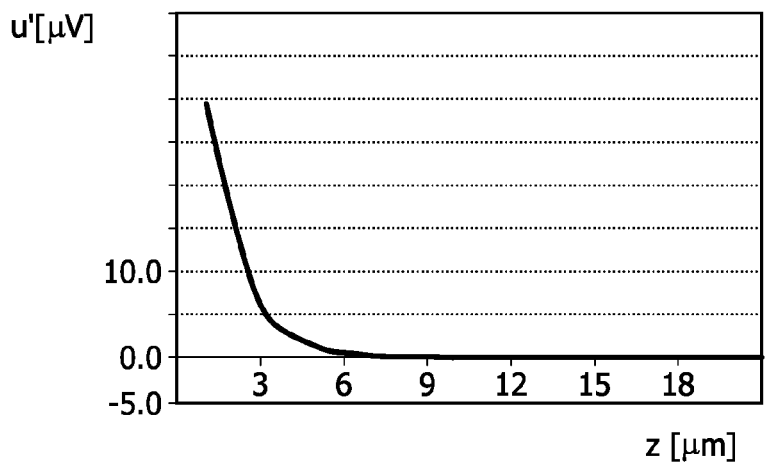
Figure 13C:
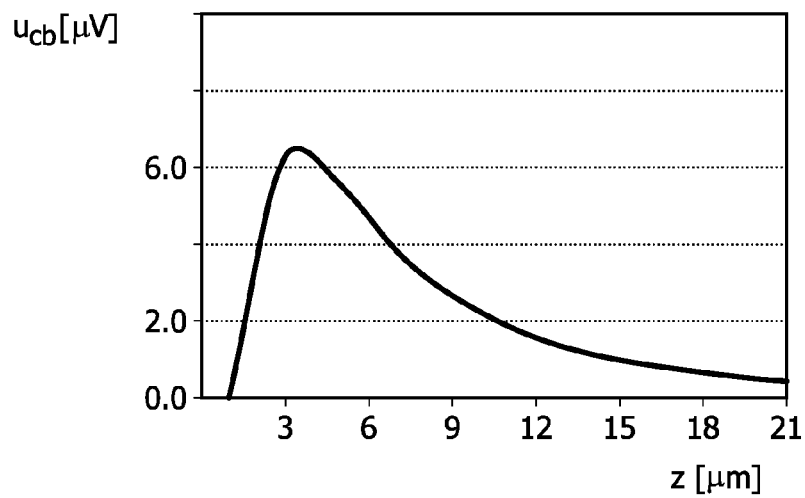

FIG. 12 shows a further magnetic sensor device 600 which comprises two excitation wires W1 and W2 on both sides of a GMR element SE and an exclusion zone 613 half-way the sensor. In the first state of FIG. 12 a), the excitation currents through the wires W1, W2 are applied in the same direction, while they are anti-parallel in the second state of FIG. 12 b). FIGS. 13 a) and b) show the corresponding normalized GMR voltages u and u', respectively (same parameters as in FIG. 7).

By sequential switching between these two states and by a weighted subtraction of the GMR voltages u, u' according to equation (14-1) with a factor $\alpha$=2.19, the combined signal $u_{cb}$ of FIG. 13 c) is achieved which shows a sensitive volume between 2-4 µm above the sensor. The value of cc depends in this case on the geometry and the position of the exclusion zone 613. It can be calibrated prior to the actual bio-measurement.

The same calculations as in equations (14-2) to (14-5) yield for this case the values given in (14-10).

III. Temporal Analysis Approach

Another approach to obtain information about the target particle concentrations in a first zone Z1 adjacent to the contact surface and a second zone Z2 farther within the bulk sample is based on an evaluation of the temporal course of a sensor signal, particularly on a measurement of the stochastic properties of the noise in the sensor signal. This can be realized by e.g. measuring the noise amplitude (power) and frequency content of the demodulated noise at the sensor output minus the thermal noise level.

In the following explanations, the sensor response to free target particles (e.g. magnetic labels) that are not bound to the contact surface is considered as noise whereas the response to bound target particles is considered as the signal one is interested in. Due to the fact that target particles move into and out the sensitivity volume of a sensor element by thermal motion, fluctuations arise, which give the noise process its stochastic nature. The proposed approach is based on the understanding that thermal or Brownian motion of a target particle depends on its size (diameter), the viscosity of the liquid and the liquid temperature, and that it is a stationary stochastic process having a characteristic (average) velocity.

While the properties of the noise arising from Brownian motion of magnetic target particles as measured by a magnetic sensor device like that described above will now be discussed, the described methods are not limited to this but are also applicable to e.g. optical sensors.

FIG. 15 illustrates a first particular realization of the temporal analysis approach, in which an estimate of the density of free target particle labels in the sensor sensitivity volume can be obtained from the difference between the sensor-signal s at the end of the assay and the sensor-signal s' after washing. Due to thermal motion, target particles or beads migrate into and out of the sensitivity volume, giving rise to noise in the sensor-signal u. On average, however, particles do not move; therefore the average number $<N_s>$ of free target particles in a sensitivity volume above the sensor is simply a fraction of the total number $N_{tot}$ of free target particles in the sample chamber. If a uniform particle distribution is assumed, this average number is given according to equation (18-1) of FIG. 18, where $V_s$ and $V_{tot}$ are the volumes of the sensitivity region and the total volume, respectively.

All particles move independently and without memory of previous positions or trajectories. The probability of finding $N_s$ particles in the sensitivity volume can be characterized as a spatial Poisson process. Therefore the average sensor response to moving target particles within the volume above the sensor is proportional to the density of these free target particles within that volume. It should be noted that this linear relation also holds if the sensor response function is not uniform in the sensitivity volume; in this case the sensor output simply equals the average number of target particles in the sensitivity volume scaled by the average sensor response.

By subtracting the sensor-signal s' after washing (i.e. removing unbound target particles from the sensor surface), which relates purely to the surface-bound target particles, from the sensor-signal s obtained at the end of the biological assay, which relates to both the signal (surface-bound target particles) and the noise average, an estimate of the density of target particles in the sensor sensitivity volume can be obtained. In FIG. 15 the application of this procedure to an endpoint measurement is sketched, however it is obvious that the method can also be applied to kinetic assays.

It should be noted that a halfway exclusion zone (cf. FIG. 12) can also be realized such that exclusively the signal from the moving particles can be measured without measuring the bound target particles. This method allows determining the noise average in a single step.

If the free target particles within the sensor volume are uniformly distributed, then the total particle density is obtained by scaling the density of free particle labels in the sensor sensitivity volume according to the volume ratios, as described above. However, in practice the uniformity may be distorted due to magnetic actuation, which effectively increases the bead density close to the sensor surface.

In another particular realization of the temporal analysis approach, an estimate of the density of target particles in the sensor sensitivity volume can be obtained from the power of the noise in the sensor response during the biological assay.

All particles move independently and without memory of previous positions or trajectories. Assuming that a target particle is able to enter and leave the sensitivity volume within two successive observation instances, then the probability of finding $N_s$ particles in the sensitivity volume is characterized as a spatial Poisson process. The variance of the number of beads in the sensitivity volume then equals $\sigma^2_N = N_s$ and therefore the noise power is proportional to $N_s$ as well.

It should be noted that this linear relation also holds if the sensor response is not uniform within the volume above the sensor, since the noise power simply scales with the variance of the sensor response.

The kinetics of particle binding to the contact surface of a biosensor is extremely slow compared to the fluctuation of the number of particles within the sensitivity zone. As a consequence, the signal from the bound particles is easily separated from the noise by frequency domain filtering. Using a high pass filter, only the noise remains and the noise power can be measured.

By subtracting the thermal noise power that is measured prior to a biological assay from the noise power in the sensor response during the assay, an estimate of the density of target particles can be obtained.

In a further particular realization of the temporal analysis approach, information on the amount of clustered target particles (beads) can be obtained by comparing the average number of target particles in the sensor sensitivity volume to the variance of the number of target particles.

For a spatial Poisson process, the mean and variance are equal. If there are both single beads and bead clusters present in the sensor sensitivity zone, then a discrepancy from the true spatial Poisson process arises. The movement of clusters into and out of the sensing zone results in a spreading of the probability distribution, since the tail values of the distribution are enlarged while the mean is lowered. Hence effectively the noise variance is increased due to the presence of clusters, which is illustrated in FIG. 16.

Information on the amount of clusters can be obtained by determining the ratio of the noise average and variance, cf. equation (18-2).

The presence of noise in the sensor-signal can also be used as a basis to determine if the biosensor is obscured in any way, e.g. by an air bubble. Evidently, if an air bubble is present in the biosensor, target particles from the sample fluid may not reach the surface and proper operation of the sensor is impossible. The absence of bulk noise indicates that no target particles are present in proximity of the sensor surface.

In addition, quantification of the free target particle density also enables a method to detect whether sufficient labels are present. For example, when beads are stored in a biosensor, they may not disperse properly into the sample volume. The noise properties can be used to determine if sufficient labels are present, and hence if the sensor operates properly.

In the following it will be shown that the diffusion coefficient of target particles (e.g. superparamagnetic labels) can be estimated from the noise power spectral density function. In an equilibrium situation, the emigration and immigration rates for beads entering and leaving the sensor sensitivity zone are equal. The migration process can be characterized by the autocorrelation function of the fluctuation of the number of beads in the sensitivity volume. The autocorrelation function can be expressed as in equation (18-3), where the variance of the number of free beads in the sensitivity volume equals $\sigma^2_N = N_s$, and $\tau$ is the time-constant of the system. The time-constant $\tau$ corresponds to the diffusion time of the sensitivity volume. Generally, Brownian motion is characterized by the mean-squared displacement in a certain observation time $\Delta t$. The mean-squared displacement in three dimensions is given in equation (18-4), where D is the diffusion coefficient. Then for a cubic sensitivity volume with edge length r, the diffusion time-constant is given in equation (18-5).

The above considerations are not limited to a cubic sensitivity volume. For differently shaped volumes, different diffusion time-constants can be obtained. For example, in general the sensitivity volume of a magnetic biosensor is not cubic, but rather a flat box with a relatively small height h compared to the sensitivity surface. Consequently, bead label migration primarily occurs orthogonal to the sensor surface, thus the time-constant in this direction is dominant. The time-constant associated with this one dimensional model can then be described by equation (18-6).

The noise power spectral density function (psdf) equals the Fourier transform of the autocorrelation function, which has the Lorentz-form of FIG. 17 and equation (18-7). Consequently, the time-constant can be determined by fitting the model psdf to the measured power spectrum and optimizing for the unknown parameter τ. For example the −3 dB point, i.e. the frequency where the normalized power density has dropped to 0.5 (cf. FIG. 17), can be used as a basis for measuring the time-constant.

It should be noted that also the psdf of the noise in the sensor signal has the Lorentz-form. If the sensor response is not uniform in the sensitivity volume, the noise psdf is simply scaled by the sensor response.

While the invention was described above with reference to particular embodiments, various modifications and extensions are possible, for example:

The sensor element can be any suitable sensor to detect the presence of target particles on or near to a sensor surface, based on any property of the particles, e.g. it can detect via magnetic methods, optical methods (e.g. imaging, fluorescence, chemiluminescence, absorption, scattering, surface plasmon resonance, Raman, etc.), sonic detection (e.g. surface acoustic wave, bulk acoustic wave, cantilever, quartz crystal etc), electrical detection (e.g. conduction, impedance, amperometric, redox cycling), etc.

The magnetic sensor can be any suitable sensor based on the detection of the magnetic properties of the particle on or near to a sensor surface, e.g. a coil, magneto-resistive sensor, magneto-restrictive sensor, Hall sensor, planar Hall sensor, flux gate sensor, SQUID, magnetic resonance sensor, etc.

In addition to molecular assays, also larger moieties can be detected with sensor devices according to the invention, e.g. cells, viruses, or fractions of cells or viruses, tissue extract, etc.

The detection can occur with or without scanning of the sensor element with respect to the sensor surface.

Measurement data can be derived as an end-point measurement, as well as by recording signals kinetically or intermittently.

The particles serving as labels can be detected directly by the sensing method. As well, the particles can be further processed prior to detection. An example of further processing is that materials are added or that the (bio) chemical or physical properties of the label are modified to facilitate detection.

The device and method can be used with several biochemical assay types, e.g. binding/unbinding assay, sandwich assay, competition assay, displacement assay, enzymatic assay, etc. It is especially suitable for DNA detection because large scale multiplexing is easily possible and different oligos can be spotted via ink-jet printing on the optical substrate.

The device and method are suited for sensor multiplexing (i.e. the parallel use of different sensors and sensor surfaces), label multiplexing (i.e. the parallel use of different types of labels) and chamber multiplexing (i.e. the parallel use of different reaction chambers).

The device and method can be used as rapid, robust, and easy to use point-of-care biosensors for small sample volumes. The reaction chamber can be a disposable item to be used with a compact reader, containing the one or more field generating means and one or more detection means. Also, the device, methods and systems of the present invention can be used in automated high-throughput testing. In this case, the reaction chamber is e.g. a well-plate or cuvette, fitting into an automated instrument.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A sensor device for determining an amount of target particles at a contact surface of a sample chamber in which a sample with said target particles can be provided, comprising:
   a sensor element for detecting the target particles in the sample chamber and for providing at least one sensor signal; and
   an evaluation unit for directly or indirectly determining the amount of target particles in a first zone immediately at the contact surface and in a second zone a distance away from the contact surface based on the at least one sensor signal,
   wherein the contact surface comprises binding sites for specifically binding the target particles,
   wherein the sensor element provides at least two sensor signals that are in a different way sensitive for the amount of target particles in the first zone and the second zone, respectively, and
   wherein a first sensor signal of the at least two sensor signals is measured with a sensitivity which is higher in the first zone than in the second zone, and a second sensor signal of the at least two sensor signals is measured with a sensitivity which is lower in the first zone than in the second zone.

2. The sensor device according to claim 1, wherein the evaluation unit determines a weighted difference of the at least two sensor signals.

3. The sensor device according to claim 1, wherein the sample chamber comprises an exclusion zone adjacent to a part of the contact surface that cannot be entered by the target particles.

4. The sensor device according to claim 1, wherein the sensor element comprises:
   at least one light source for emitting two input light beams such that they are totally internally reflected at the contact surface as corresponding output light beams under different conditions, whereby evanescent waves are generated during the total internal reflection of the two input light beams at the contact surface that have different decay distances, whereby the two input light beams have different spectral composition and/or angles of incidence at the contact surface;
   at least one light detector for determining the amount of light of the output light beams and for providing the sensor signals.

5. A sensor device for determining an amount of target particles at a contact surface of a sample chamber in which a sample with said target particles can be provided, comprising:
   a sensor element for detecting the target particles in the sample chamber and for providing at least one sensor signal;

an evaluation unit for directly or indirectly determining the amount of target particles in a first zone immediately at the contact surface and in a second zone a distance away from the contact surface based on the at least one sensor-signal;

at least one magnetic field generator for generating at least two magnetic excitation fields of different configuration in the sample chamber, whereby the magnetic field generator comprises at least two conductor wires that can selectively be supplied with excitation currents and that have different geometrical arrangements with respect to the magnetic sensor element; and a magnetic sensor element for detecting magnetic reaction fields generated by magnetic target particles in reaction to the magnetic excitation fields and for providing the sensor-signals.

6. A sensor device for determining an amount of target particles at a contact surface of a sample chamber in which a sample with said target particles can be provided, comprising:

a sensor element for detecting the target particles in the sample chamber and for providing at least one sensor signal;

an evaluation unit for directly or indirectly determining the amount of target particles in a first zone immediately at the contact surface and in a second zone a distance away from the contact surface based on the at least one sensor-signal; and pairs of conductor wires that are arranged symmetrically with respect to a magnetic sensor element, wherein the contact surface comprises binding sites to which target particles can bind.

7. A sensor device for determining an amount of target particles at a contact surface of a sample chamber in which a sample with said target particles can be provided, comprising:

a sensor element for detecting the target particles in the sample chamber and for providing at least one sensor signal;

an evaluation unit for directly or indirectly determining the amount of target particles in a first zone immediately at the contact surface and in a second zone a distance away from the contact surface based on the at least one sensor-signal; and a manipulation comprising a magnetic field generator for actively moving the target particles, wherein the manipulation device is configured to remove free target particles from a sensitive region of the sensor element.

8. A sensor device for determining an amount of target particles at a contact surface of a sample chamber in which a sample with said target particles can be provided, comprising:

a sensor element for detecting the target particles in the sample chamber and for providing at least one sensor signal; and an evaluation unit for directly or indirectly determining the amount of target particles in a first zone immediately at the contact surface and in a second zone a distance away from the contact surface based on the at least one sensor-signal, wherein the evaluation unit is configured to perform an evaluation of a temporal course of the sensor signal, the evaluation takes place with respect to stochastic movements of the target particles, and/or wherein the evaluation unit is configured to determine a noise power of the sensor signal after a high-pass filtering, and/or wherein the evaluation unit is configured to determine an average number of the target particles in the second zone and a variance of the average number, and/or wherein the evaluation unit is configured to infer information about an amount of clustered target particles, about a coverage of the contact surface, and/or about diffusion characteristics of the target particles.

9. A method for determining an amount of target particles at a contact surface adjacent to a sample chamber in which a sample with said target particles is provided, comprising the acts of:

detecting the target particles in the sample chamber;

providing at least one sensor signal with a sensor element;

directly or indirectly determining with an evaluation unit the amount of target particles in a first zone immediately at the contact surface and a second zone a distance away from the contact surface based on the at least one sensor signal; and providing at least two sensor signals that are in a different way sensitive to the amount of target particles in the first zone and the second zone, respectively, wherein the contact surface comprises binding sites for specifically binding the target particles, wherein a first sensor signal of the at least two sensor signals is measured with a sensitivity which is higher in the first zone than in the second zone, and a second sensor signal of the at least two sensor signals is measured with a sensitivity which is lower in the first zone than in the second zone.

10. The method according to claim 9, further comprising the act of deriving the sensor signals from a frustrated total internal reflection with evanescent waves of different decay distances.

11. A method for determining an amount of target particles at a contact surface adjacent to a sample chamber in which a sample with said target particles is provided, comprising the acts of:

detecting the target particles in the sample chamber;

providing at least one sensor signal with a sensor element;

directly or indirectly determining with an evaluation unit the amount of target particles in a first zone immediately at the contact surface and a second zone a distance away from the contact surface based on the at least one sensor signal; and deriving the at least one sensor signal from magnetic reaction fields of magnetic target particles that were excited with magnetic excitation fields of different configurations.

12. A method for determining an amount of target particles at a contact surface adjacent to a sample chamber in which a sample with said target particles is provided, comprising the acts of:

detecting the target particles in the sample chamber;

providing at least one sensor signal with a sensor element;

directly or indirectly determining with an evaluation unit the amount of target particles in a first zone immediately at the contact surface and a second zone a distance away from the contact surface based on the at least one sensor signal; and evaluating a temporal course of the sensor signal with respect to stochastic movements of the target particles.

13. Use of the sensor device according to claim 1 for molecular diagnostics, biological sample analysis, or chemical sample analysis.

* * * * *